United States Patent
Hyland et al.

(10) Patent No.: US 10,262,518 B2
(45) Date of Patent: *Apr. 16, 2019

(54) METHOD OF DISSEMINATING MONITORING INFORMATION RELATING TO CONTAMINATION AND CORROSION WITHIN AN INFRASTRUCTURE

(71) Applicant: Mueller International, LLC, Atlanta, GA (US)

(72) Inventors: Gregory E. Hyland, Atlanta, GA (US); Robert Paul Keefe, Alpharetta, GA (US); Marietta Edmonds Zakas, Atlanta, GA (US); Clayton Robert Barker, Atlanta, GA (US)

(73) Assignee: Mueller International LLC, Atlanta, GA (US)

(*) Notice: Subject to any disclaimer, the term of this patent is extended or adjusted under 35 U.S.C. 154(b) by 0 days.

This patent is subject to a terminal disclaimer.

(21) Appl. No.: 15/895,062

(22) Filed: Feb. 13, 2018

(65) Prior Publication Data

US 2018/0174424 A1 Jun. 21, 2018

Related U.S. Application Data

(63) Continuation of application No. 14/928,725, filed on Oct. 30, 2015, now Pat. No. 9,934,670, which is a (Continued)

(51) Int. Cl.
*G01N 21/94* (2006.01)
*G01N 33/00* (2006.01)
(Continued)

(52) U.S. Cl.
CPC ............ *G08B 21/18* (2013.01); *G01N 21/94* (2013.01); *G01N 33/0075* (2013.01);
(Continued)

(58) Field of Classification Search
CPC ....... A62C 35/58; A62C 35/645; A62C 35/68; G01F 1/666; G01H 3/12; G01N 21/94;
(Continued)

(56) References Cited

U.S. PATENT DOCUMENTS 3,705,385 A 12/1972 Batz
4,093,997 A 6/1978 Germer
(Continued)

FOREIGN PATENT DOCUMENTS

AU 2009308949 5/2010
AU 2010249499 5/2015
(Continued)

OTHER PUBLICATIONS

Clark, Kenneth A.; Issue Notification for U.S. Appl. No. 14/209,257, filed Mar. 13, 2014, dated Sep. 26, 2018, 1 pg.
(Continued)

*Primary Examiner* — Quan-Zhen Wang
*Assistant Examiner* — Stephen R Burgdorf
(74) *Attorney, Agent, or Firm* — Taylor English Duma LLP

(57) ABSTRACT

A method of disseminating information includes detecting, by a first monitoring device, a condition of an aspect of an infrastructure; transmitting data relating to the condition and a first time stamp; detecting, by a second monitoring device, the condition; transmitting data relating to the condition and a second time stamp; determining whether a difference in data indicates a problem of contamination; subsequent to an indication of the problem of contamination, determining an amount of the contamination, an approximate location of the contamination, a direction of contamination movement, and a speed of the contamination movement, based on the first time stamp and the second time stamp; determining whether a difference in data indicates corrosion within the infrastruc-
(Continued)

ture; and subsequent to the indication of corrosion, determining whether the data relating to the condition indicates an amount of corrosion determined to be the problem, and a level of severity of the corrosion.

7 Claims, 1 Drawing Sheet

Related U.S. Application Data continuation of application No. 12/606,957, filed on Oct. 27, 2009, now Pat. No. 9,202,362.

(60) Provisional application No. 61/108,770, filed on Oct. 27, 2008, provisional application No. 61/180,600, filed on May 22, 2009.

(51) Int. Cl.
 G08B 21/18 (2006.01)
 G08B 25/00 (2006.01)
 G08B 25/08 (2006.01)
 H04M 11/04 (2006.01)

(52) U.S. Cl.
 CPC ........... *G08B 25/009* (2013.01); *G08B 25/08* (2013.01); *H04M 11/04* (2013.01)

(58) Field of Classification Search
 CPC ............... G01N 29/4429; G01N 33/00; G01N 33/0075; G01Q 10/06; G08B 21/18; G08B 25/00; G08B 25/009; G08B 25/08; H04M 11/04
 USPC ........................................................ 340/517
 See application file for complete search history.

(56) References Cited

U.S. PATENT DOCUMENTS

| | | |
|---|---|---|
| 4,120,031 A | 10/1978 | Kincheloe et al. |
| 4,282,413 A | 8/1981 | Simons |
| 4,291,375 A | 9/1981 | Wolf |
| 4,388,690 A | 6/1983 | Lumsden |
| 4,414,633 A | 11/1983 | Churchill |
| 4,442,492 A | 4/1984 | Karlsson et al. |
| 4,465,970 A | 8/1984 | Dimassimo et al. |
| 4,516,213 A | 5/1985 | Gidden |
| 4,542,469 A | 9/1985 | Brandberry et al. |
| 4,591,988 A | 5/1986 | Klima et al. |
| 4,705,060 A | 11/1987 | Goulbourne |
| 4,707,852 A | 11/1987 | Jahr et al. |
| 4,727,900 A | 3/1988 | Dooling et al. |
| 4,792,946 A | 12/1988 | Mayo |
| 4,803,632 A | 2/1989 | Frew et al. |
| 4,833,618 A | 5/1989 | Verma et al. |
| 4,868,566 A | 9/1989 | Strobel et al. |
| 4,881,070 A | 11/1989 | Burrowes et al. |
| 4,940,976 A | 7/1990 | Gastouniotis et al. |
| 4,945,344 A | 7/1990 | Farrell |
| 4,989,830 A | 2/1991 | Ratnik |
| 5,056,107 A | 10/1991 | Johnson et al. |
| 5,075,792 A | 12/1991 | Brown et al. |
| 5,079,715 A | 1/1992 | Venkataraman et al. |
| 5,121,344 A | 6/1992 | Laage et al. |
| 5,239,575 A | 8/1993 | White et al. |
| 5,298,894 A | 3/1994 | Cerny |
| 5,327,925 A | 7/1994 | Ortel |
| 5,381,136 A | 1/1995 | Powers et al. |
| 5,434,911 A | 7/1995 | Gray et al. |
| 5,438,329 A | 8/1995 | Gastouniotis et al. |
| 5,451,938 A | 9/1995 | Brennan, Jr. |
| 5,459,459 A | 10/1995 | Lee, Jr. |
| 5,481,259 A | 1/1996 | Bane |
| 5,493,287 A | 2/1996 | Bane |
| 5,525,898 A | 6/1996 | Lee et al. |
| 5,553,094 A | 9/1996 | Johnson et al. |
| 5,588,462 A | 12/1996 | McHugh |
| 5,590,179 A | 12/1996 | Shincovich et al. |
| 5,594,740 A | 1/1997 | Ladue |
| 5,617,084 A | 4/1997 | Sears |
| 5,631,554 A | 5/1997 | Briese et al. |
| 5,646,863 A | 7/1997 | Morton |
| 5,654,692 A | 8/1997 | Baxter, Jr. et al. |
| 5,673,252 A | 9/1997 | Johnson et al. |
| 5,708,195 A | 1/1998 | Kurisu et al. |
| 5,714,931 A | 2/1998 | Petite |
| 5,748,104 A | 5/1998 | Argyroudis et al. |
| 5,751,797 A | 5/1998 | Saadeh |
| 5,801,643 A | 9/1998 | Williams et al. |
| 5,815,086 A | 9/1998 | Ivie et al. |
| 5,852,658 A | 12/1998 | Knight et al. |
| 5,877,703 A | 3/1999 | Bloss et al. |
| 5,892,758 A | 4/1999 | Argyroudis |
| 5,907,491 A | 5/1999 | Canada et al. |
| 5,924,051 A | 7/1999 | Provost et al. |
| 5,926,103 A | 7/1999 | Petite |
| 5,926,531 A | 7/1999 | Petite |
| 5,940,009 A | 8/1999 | Loy et al. |
| 5,963,146 A | 10/1999 | Johnson et al. |
| 5,971,011 A | 10/1999 | Price |
| 5,993,739 A | 11/1999 | Lyon |
| 5,994,892 A | 11/1999 | Turino et al. |
| 6,006,212 A | 12/1999 | Schleich et al. |
| 6,028,522 A | 2/2000 | Petite |
| 6,031,455 A | 2/2000 | Grube et al. |
| 6,044,062 A | 3/2000 | Brownrigg et al. |
| 6,058,374 A | 5/2000 | Guthrie et al. |
| 6,060,994 A | 5/2000 | Chen |
| 6,078,269 A | 6/2000 | Markwell |
| 6,081,204 A | 6/2000 | Lavoie et al. |
| 6,163,276 A | 12/2000 | Irving et al. |
| 6,172,616 B1 | 1/2001 | Johnson et al. |
| 6,194,902 B1 | 2/2001 | Kuo |
| 6,195,018 B1 | 2/2001 | Ragle et al. |
| 6,218,953 B1 | 4/2001 | Petite |
| 6,233,327 B1 | 5/2001 | Petite |
| 6,246,677 B1 | 6/2001 | Nap et al. |
| 6,249,516 B1 | 6/2001 | Brownrigg et al. |
| 6,288,641 B1 | 9/2001 | Casais |
| 6,317,051 B1 | 11/2001 | Cohen |
| 6,333,975 B1 | 12/2001 | Brunn et al. |
| 6,373,399 B1 | 4/2002 | Johnson et al. |
| 6,392,538 B1 | 5/2002 | Shere |
| 6,424,270 B1 | 7/2002 | Ali |
| 6,430,268 B1 | 8/2002 | Petite |
| 6,437,692 B1 | 8/2002 | Petite et al. |
| 6,453,247 B1 | 9/2002 | Hunaidi |
| 6,456,197 B1 | 9/2002 | Lauritsen et al. |
| 6,470,903 B2 | 10/2002 | Reyman |
| 6,493,377 B2 | 12/2002 | Schilling et al. |
| 6,512,463 B1 | 1/2003 | Campbell et al. |
| 6,528,957 B1 | 3/2003 | Luchaco |
| 6,538,577 B1 | 3/2003 | Ehrke et al. |
| 6,560,543 B2 | 5/2003 | Wolfe et al. |
| 6,564,159 B1 | 5/2003 | Lavoie et al. |
| 6,577,961 B1 | 6/2003 | Hubbard et al. |
| 6,618,578 B1 | 9/2003 | Petite |
| 6,624,750 B1 | 9/2003 | Marman et al. |
| 6,628,207 B1 | 9/2003 | Hemminger et al. |
| 6,628,764 B1 | 9/2003 | Petite |
| 6,633,781 B1 | 10/2003 | Lee et al. |
| 6,653,945 B2 | 11/2003 | Johnson et al. |
| 6,657,552 B2 | 12/2003 | Belski et al. |
| 6,675,071 B1 | 1/2004 | Griffin, Jr. et al. |
| 6,675,834 B1 | 1/2004 | Lai |
| 6,677,861 B1 | 1/2004 | Henry et al. |
| 6,710,721 B1 | 3/2004 | Holowick |
| 6,747,557 B1 | 6/2004 | Petite et al. |
| 6,798,352 B2 | 9/2004 | Holowick |
| 6,816,072 B2 | 11/2004 | Zoratti |
| 6,836,737 B2 | 12/2004 | Petite et al. |
| 6,847,300 B2 | 1/2005 | Yee et al. |

(56) References Cited

U.S. PATENT DOCUMENTS

| | | |
|---|---|---|
| 6,891,477 B2 * | 5/2005 | Aronstam ............... E21B 47/12 340/606 |
| 6,891,838 B1 | 5/2005 | Petite et al. |
| 6,914,533 B2 | 7/2005 | Petite |
| 6,914,893 B2 | 7/2005 | Petite |
| 6,931,445 B2 | 8/2005 | Davis |
| 6,946,972 B2 | 9/2005 | Mueller et al. |
| 6,954,701 B2 | 10/2005 | Wolfe |
| 6,954,814 B1 | 10/2005 | Leach |
| 6,972,677 B2 | 12/2005 | Coulthard |
| 6,978,210 B1 | 12/2005 | Suter et al. |
| 6,980,079 B1 | 12/2005 | Shintani |
| 7,008,239 B1 | 3/2006 | Ju |
| 7,009,530 B2 | 3/2006 | Zigdon et al. |
| 7,012,546 B1 | 3/2006 | Zigdon et al. |
| 7,020,701 B1 | 3/2006 | Gelvin |
| 7,042,368 B2 | 5/2006 | Patterson et al. |
| 7,053,767 B2 | 5/2006 | Petite et al. |
| 7,054,271 B2 | 5/2006 | Brownrigg |
| 7,061,924 B1 | 6/2006 | Durrant et al. |
| 7,072,945 B1 | 7/2006 | Nieminen et al. |
| 7,079,810 B2 | 7/2006 | Petite et al. |
| 7,088,239 B2 | 8/2006 | Basinger et al. |
| 7,089,125 B2 | 8/2006 | Sonderegger |
| 7,103,511 B2 | 9/2006 | Petite |
| 7,117,051 B2 | 10/2006 | Landry et al. |
| 7,124,184 B2 | 10/2006 | Chung et al. |
| 7,137,550 B1 | 11/2006 | Petite |
| 7,142,107 B2 | 11/2006 | Kates |
| 7,248,181 B2 | 7/2007 | Patterson et al. |
| 7,256,704 B2 | 8/2007 | Yoon et al. |
| 7,263,073 B2 | 8/2007 | Petite et al. |
| 7,292,143 B2 | 11/2007 | Drake et al. |
| 7,295,128 B2 | 11/2007 | Petite |
| 7,301,456 B2 | 11/2007 | Han |
| 7,315,257 B2 | 1/2008 | Patterson et al. |
| 7,342,504 B2 | 3/2008 | Crane et al. |
| 7,353,280 B2 | 4/2008 | Chiles et al. |
| 7,356,614 B2 | 4/2008 | Kim et al. |
| 7,363,031 B1 | 4/2008 | Aisa |
| 7,397,907 B1 | 7/2008 | Petite |
| 7,417,557 B2 | 8/2008 | Osterloh et al. |
| 7,423,985 B1 | 9/2008 | Hill |
| 7,424,527 B2 | 9/2008 | Petite |
| 7,443,313 B2 | 10/2008 | Davis et al. |
| 7,444,401 B1 | 10/2008 | Keyghobad |
| 7,453,373 B2 | 11/2008 | Cumeralto et al. |
| 7,468,661 B2 | 12/2008 | Petite et al. |
| 7,478,108 B2 | 1/2009 | Townsend et al. |
| 7,480,501 B2 | 1/2009 | Petite |
| 7,497,957 B2 | 3/2009 | Bernard |
| 7,526,539 B1 | 4/2009 | Hsu |
| 7,550,746 B2 | 6/2009 | Tokhtuev et al. |
| 7,650,425 B2 | 1/2010 | Davis |
| 7,697,492 B2 | 4/2010 | Petite |
| 7,739,378 B2 | 6/2010 | Petite |
| 7,752,309 B2 | 7/2010 | Keyghobad |
| 7,756,086 B2 | 7/2010 | Petite |
| 7,767,093 B2 | 8/2010 | Frank |
| 7,783,738 B2 | 8/2010 | Keyghobad |
| 7,792,946 B2 | 9/2010 | Keyghobad |
| 7,870,080 B2 | 1/2011 | Budike, Jr. |
| 7,880,641 B2 | 2/2011 | Parris et al. |
| 7,920,983 B1 | 4/2011 | Peleg |
| 7,980,317 B1 | 7/2011 | Preta et al. |
| 8,082,945 B1 | 12/2011 | White et al. |
| 8,109,131 B2 | 2/2012 | Winter |
| 8,140,667 B2 | 3/2012 | Keyghobad et al. |
| 8,249,042 B2 | 8/2012 | Sparr et al. |
| 8,351,409 B2 | 1/2013 | Albert et al. |
| 8,407,333 B2 | 3/2013 | Keyghobad |
| 8,549,131 B2 | 10/2013 | Keyghobad et al. |
| 8,615,374 B1 * | 12/2013 | Discenzo ............... G06F 15/00 219/497 |
| 8,823,509 B2 | 9/2014 | Hyland et al. |
| 9,202,362 B2 | 12/2015 | Hyland et al. |
| 9,604,858 B2 | 3/2017 | Kamen et al. |
| 9,934,670 B2 | 4/2018 | Hyland et al. |
| 10,180,414 B2 | 1/2019 | Clark et al. |
| 10,203,315 B2 | 2/2019 | Clark et al. |
| 2001/0010032 A1 | 7/2001 | Ehlers et al. |
| 2001/0013488 A1 | 8/2001 | Fukunaga et al. |
| 2001/0024163 A1 | 9/2001 | Petite |
| 2001/0048030 A1 | 12/2001 | Sharood et al. |
| 2002/0002425 A1 | 1/2002 | Dossey et al. |
| 2002/0013679 A1 | 1/2002 | Petite |
| 2002/0019725 A1 | 2/2002 | Petite |
| 2002/0031101 A1 | 3/2002 | Petite |
| 2002/0043969 A1 | 4/2002 | Duncan |
| 2002/0062392 A1 | 5/2002 | Nishikawa et al. |
| 2002/0067717 A1 | 6/2002 | Raschke et al. |
| 2002/0073183 A1 | 6/2002 | Yoon et al. |
| 2002/0089802 A1 | 7/2002 | Beckwith |
| 2002/0105346 A1 | 8/2002 | Banks |
| 2002/0130069 A1 | 9/2002 | Moskoff |
| 2002/0130768 A1 | 9/2002 | Che et al. |
| 2002/0149487 A1 | 10/2002 | Haines |
| 2002/0169643 A1 | 11/2002 | Petite et al. |
| 2002/0190956 A1 | 12/2002 | Klein et al. |
| 2003/0009515 A1 | 1/2003 | Lee et al. |
| 2003/0018733 A1 | 1/2003 | Yoon et al. |
| 2003/0018776 A1 | 1/2003 | Yoon et al. |
| 2003/0036810 A1 | 2/2003 | Petite |
| 2003/0046377 A1 | 3/2003 | Daum et al. |
| 2003/0074109 A1 | 4/2003 | Jeong et al. |
| 2003/0093484 A1 | 5/2003 | Petite |
| 2003/0107485 A1 | 6/2003 | Zoratti |
| 2003/0174070 A1 | 9/2003 | Garrod et al. |
| 2004/0006513 A1 | 1/2004 | Wolfe |
| 2004/0010561 A1 | 1/2004 | Kim |
| 2004/0054747 A1 | 3/2004 | Breh |
| 2004/0064217 A1 | 4/2004 | Addink et al. |
| 2004/0129312 A1 | 7/2004 | Cuzzo et al. |
| 2004/0138840 A1 | 7/2004 | Wolfe |
| 2004/0139210 A1 | 7/2004 | Lee et al. |
| 2004/0154965 A1 | 8/2004 | Baum et al. |
| 2004/0158333 A1 | 8/2004 | Ha et al. |
| 2004/0159149 A1 | 8/2004 | Williams et al. |
| 2004/0183687 A1 | 9/2004 | Petite et al. |
| 2004/0199340 A1 | 10/2004 | Kersey et al. |
| 2004/0212510 A1 * | 10/2004 | Aronstam ............... E21B 47/12 340/606 |
| 2005/0009192 A1 | 1/2005 | Page |
| 2005/0084418 A1 | 4/2005 | Hill et al. |
| 2005/0096753 A1 | 5/2005 | Arling |
| 2005/0104747 A1 | 5/2005 | Silic et al. |
| 2005/0120778 A1 * | 6/2005 | Von Herzen ........... G01N 33/18 73/61.41 |
| 2005/0159823 A1 | 7/2005 | Hayes |
| 2005/0195768 A1 | 9/2005 | Petite et al. |
| 2005/0195775 A1 | 9/2005 | Petite et al. |
| 2005/0201379 A1 | 9/2005 | Zhang et al. |
| 2005/0201397 A1 | 9/2005 | Petite |
| 2005/0203647 A1 | 9/2005 | Landry et al. |
| 2005/0247114 A1 | 11/2005 | Kahn |
| 2005/0251367 A1 | 11/2005 | Kahn et al. |
| 2006/0028355 A1 | 2/2006 | Patterson et al. |
| 2006/0031040 A1 | 2/2006 | Wolfe |
| 2006/0041655 A1 | 2/2006 | Holloway et al. |
| 2006/0046664 A1 | 3/2006 | Paradiso et al. |
| 2006/0059977 A1 | 3/2006 | Kates |
| 2006/0098576 A1 | 5/2006 | Brownrigg et al. |
| 2006/0122736 A1 | 6/2006 | Alexanian |
| 2006/0158347 A1 | 7/2006 | Roche et al. |
| 2006/0174707 A1 | 8/2006 | Zhang |
| 2006/0181414 A1 | 8/2006 | Bandy et al. |
| 2006/0197345 A1 | 9/2006 | Kuroki et al. |
| 2006/0201550 A1 | 9/2006 | Blyth et al. |
| 2006/0218266 A1 | 9/2006 | Matsumoto et al. |
| 2006/0248961 A1 | 11/2006 | Shachar |
| 2006/0272830 A1 | 12/2006 | Fima |
| 2006/0273896 A1 | 12/2006 | Kates |
| 2007/0035315 A1 | 2/2007 | Hilleary |
| 2007/0052540 A1 | 3/2007 | Hall et al. |

(56) References Cited

U.S. PATENT DOCUMENTS

| | | |
|---|---|---|
| 2007/0059986 A1 | 3/2007 | Rockwell |
| 2007/0063866 A1 | 3/2007 | Webb |
| 2007/0090059 A1 | 4/2007 | Plummer |
| 2007/0219728 A1 | 9/2007 | Papageorgiou et al. |
| 2007/0293990 A1 | 12/2007 | Alexanian |
| 2007/0298779 A1 | 12/2007 | Wolman et al. |
| 2008/0030319 A1 | 2/2008 | McKeena et al. |
| 2008/0095403 A1 | 4/2008 | Benhammou |
| 2008/0109090 A1 | 5/2008 | Esmaili et al. |
| 2008/0122641 A1 | 5/2008 | Amidi |
| 2008/0136191 A1 | 6/2008 | Baarman et al. |
| 2008/0155064 A1 | 6/2008 | Kosuge |
| 2008/0186898 A1 | 8/2008 | Petite |
| 2008/0195329 A1 | 8/2008 | Prince et al. |
| 2008/0289402 A1 | 11/2008 | Chowdhury |
| 2008/0291054 A1 | 11/2008 | Groft |
| 2009/0040057 A1 | 2/2009 | Keyghobad |
| 2009/0066524 A1 | 3/2009 | Yukawa et al. |
| 2009/0068947 A1 | 3/2009 | Petite |
| 2009/0084734 A1 | 4/2009 | Yencho |
| 2009/0121860 A1 | 5/2009 | Kimmel et al. |
| 2009/0123340 A1 | 5/2009 | Knudsen et al. |
| 2009/0157521 A1 | 6/2009 | Moren |
| 2009/0215424 A1 | 8/2009 | Petite |
| 2009/0243840 A1 | 10/2009 | Petite et al. |
| 2009/0260697 A1 | 10/2009 | Mevius et al. |
| 2009/0287838 A1 | 11/2009 | Keyghobad et al. |
| 2009/0287966 A1 | 11/2009 | Keyghobad |
| 2009/0301571 A1 | 12/2009 | Ruhs |
| 2009/0309755 A1 | 12/2009 | Williamson et al. |
| 2009/0319853 A1 | 12/2009 | Keyghobad |
| 2010/0017465 A1 | 1/2010 | Brownrigg et al. |
| 2010/0039984 A1 | 2/2010 | Brownrigg |
| 2010/0105146 A1 | 4/2010 | Meeusen |
| 2010/0193430 A1 | 8/2010 | Whiteman |
| 2010/0194582 A1 | 8/2010 | Petite |
| 2010/0214120 A1 | 8/2010 | Means |
| 2010/0250054 A1 | 9/2010 | Petite |
| 2010/0265909 A1 | 10/2010 | Petite et al. |
| 2010/0312881 A1 | 12/2010 | Davis et al. |
| 2010/0332149 A1 | 12/2010 | Scholpp |
| 2011/0030482 A1 | 2/2011 | Meeusen et al. |
| 2011/0044276 A1 | 2/2011 | Albert et al. |
| 2011/0059462 A1 | 3/2011 | Lim et al. |
| 2011/0093123 A1 | 4/2011 | Alexanian |
| 2011/0125412 A1 | 5/2011 | Salzer et al. |
| 2011/0132484 A1 | 6/2011 | Teach et al. |
| 2011/0178644 A1 | 7/2011 | Picton |
| 2011/0190947 A1 | 8/2011 | Savelle, Jr. et al. |
| 2011/0215945 A1 | 9/2011 | Peleg et al. |
| 2011/0233935 A1 | 9/2011 | Baarman et al. |
| 2011/0257788 A1 | 10/2011 | Wiemers et al. |
| 2011/0307203 A1 | 12/2011 | Higgins |
| 2011/0308638 A1 | 12/2011 | Hyland |
| 2012/0038170 A1 | 2/2012 | Stuart et al. |
| 2012/0106518 A1 | 5/2012 | Albert et al. |
| 2012/0132445 A1 | 5/2012 | Mallon et al. |
| 2012/0191868 A1 | 7/2012 | Keyghobad |
| 2012/0271686 A1 | 10/2012 | Silverman |
| 2012/0298208 A1 | 11/2012 | Taylor et al. |
| 2012/0298381 A1 | 11/2012 | Taylor |
| 2012/0311170 A1 | 12/2012 | Keyghobad et al. |
| 2013/0036800 A1 | 2/2013 | Mohajer |
| 2013/0041601 A1 | 2/2013 | Dintakurti et al. |
| 2013/0118239 A1 | 5/2013 | Forstmeier |
| 2013/0341934 A1 | 12/2013 | Kawanishi |
| 2014/0026644 A1 | 1/2014 | Patel et al. |
| 2014/0262998 A1 | 6/2014 | Wagner et al. |
| 2014/0278246 A1 | 9/2014 | Clark et al. |
| 2014/0340238 A1 | 11/2014 | Hyland |
| 2015/0308627 A1 | 10/2015 | Hoskins |
| 2016/0049067 A1 | 2/2016 | Hyland |
| 2016/0356755 A1 | 12/2016 | Gifford |
| 2017/0059543 A1 | 3/2017 | Clark |
| 2018/0372706 A1 | 12/2018 | Clark et al. |
| 2018/0372707 A1 | 12/2018 | Clark et al. |
| 2018/0372708 A1 | 12/2018 | Clark et al. |

FOREIGN PATENT DOCUMENTS

| | | |
|---|---|---|
| AU | 2014259545 | 11/2015 |
| AU | 2015202223 | 9/2016 |
| AU | 2014235054 | 2/2018 |
| AU | 2018200410 | 1/2019 |
| CA | 2634759 | 12/2009 |
| CA | 2741843 | 5/2018 |
| CA | 2772545 | 12/2018 |
| CN | 1185838 | 6/1998 |
| CN | 204828756 | 12/2015 |
| DE | 202006017758 | 2/2007 |
| EP | 1901253 | 3/2008 |
| EP | 2433440 | 7/2018 |
| EP | 2350992 | 1/2019 |
| EP | 3422319 | 1/2019 |
| EP | 3422320 | 1/2019 |
| GB | 2305333 | 4/1997 |
| JP | 62-295674 | 12/1987 |
| JP | 05-253316 | 10/1993 |
| JP | 06-223279 | 8/1994 |
| JP | 6300606 | 10/1994 |
| JP | H0731989 | 2/1995 |
| JP | 07-116285 | 5/1995 |
| JP | 07231363 | 8/1995 |
| JP | 2008128079 | 5/1996 |
| JP | 11-046254 | 2/1999 |
| JP | 2000285356 | 10/2000 |
| JP | 2001200952 | 7/2001 |
| JP | 2002352361 | 12/2002 |
| JP | 2006285645 | 10/2006 |
| JP | 2008198044 | 8/2008 |
| JP | 2012507090 | 3/2012 |
| JP | 2012527706 | 11/2012 |
| WO | 9810299 | 3/1998 |
| WO | 9810394 | 3/1998 |
| WO | 2008087911 | 7/2008 |
| WO | 2009012254 | 1/2009 |
| WO | 2010051287 | 5/2010 |
| WO | 2010135587 | 11/2010 |
| WO | 2014151384 | 9/2014 |
| WO | 2016197096 | 12/2016 |

OTHER PUBLICATIONS

Clark, Kenneth A.; Notice of Allowance for U.S. Appl. No. 15/347,849, filed Nov. 10, 2016, dated Sep. 18, 2018, 20 pgs.

Gifford, Paul; Non-Final Office Action for U.S. Appl. No. 15/171,722, filed Jun. 2, 2016, dated Aug. 29, 2018, 16 pgs.

Hyland, Gregory E.; Applicant Initiated Interview Summary for U.S. Appl. No. 12/606,957, filed Oct. 27, 2009, dated Feb. 18, 2014, 4 pgs.

Hyland, Gregory E.; Final Office Action for U.S. Appl. No. 12/606,957, filed Oct. 27, 2009, dated Dec. 17, 2013, 54 pgs.

Hyland, Gregory E.; Final Office Action for U.S. Appl. No. 12/606,957, filed Oct. 27, 2009, dated Apr. 10, 2013, 80 pgs.

Hyland, Gregory E.; Final Office Action for U.S. Appl. No. 12/606,957, filed Oct. 27, 2009, dated Sep. 22, 2014, 49 pgs.

Hyland, Gregory E.; Issue Notification for U.S. Appl. No. 12/606,957, filed Oct. 27, 2009, dated Nov. 11, 2015, 1 pg.

Hyland, Gregory E.; Non-Final Office Action for U.S. Appl. No. 12/606,957, filed Oct. 27, 2009, dated Oct. 18, 2012; 44 pgs.

Hyland, Gregory E.; Non-Final Office Action for U.S. Appl. No. 12/606,957, filed Oct. 27, 2009, dated Apr. 8, 2014, 43 pgs.

Hyland, Gregory E.; Non-Final Office Action for U.S. Appl. No. 12/606,957, filed Oct. 27, 2009, dated Sep. 6, 2013; 53 pgs.

Hyland, Gregory E.; Non-Final Office Action for U.S. Appl. No. 12/606,957, filed Oct. 27, 2009, dated Apr. 16, 2015, 47 pgs.

Hyland, Gregory E.; Notice of Allowance for U.S. Appl. No. 12/606,957, filed Oct. 27, 2009, dated Jul. 27, 2015, 19 pgs.

Hyland, Gregory E.; Supplemental Notice of Allowability for U.S. Appl. No. 12/606,957, filed Oct. 27, 2009, dated Oct. 13, 2015, 4 pgs.

(56) References Cited

OTHER PUBLICATIONS

Hyland, Gregory E.; Final Office Action for U.S. Appl. No. 14/928,725, filed Oct. 30, 2015, dated Jul. 18, 2017, 51 pgs.
Hyland, Gregory E.; Non-final Office Action for U.S. Appl. No. 14/928,725, filed Oct. 30, 2015, dated Jan. 25, 2017, 137 pgs.
Hyland, Gregory E.; Notice of Allowance for U.S. Appl. No. 14/928,725, filed Oct. 30, 2015, dated Nov. 30, 2017, 22 pgs.
Hyland, Gregory E.; Supplemental Notice of Allowance for U.S. Appl. No. 14/928,725, filed Oct. 30, 2015, dated Dec. 28, 2017, 6 pgs.
Hyland, Gregory E.; Final Office Action for U.S. Appl. No. 12/784,300, filed May 20, 2010, dated Feb. 11, 2014; 44 pgs.
Hyland, Gregory E.; Final Office Action for U.S. Appl. No. 12/784,300, filed May 20, 2010, dated May 29, 2013, 71 pgs.
Hyland, Gregory E.; Issue Notification for U.S. Appl. No. 12/784,300, filed May 20, 2010, dated Aug. 13, 2014. 1 pg.
Hyland, Gregory E.; Non-Final Office Action for U.S. Appl. No. 12/784,300, filed May 20, 2010, dated Sep. 10, 2012, 35 pgs.
Hyland, Gregory E.; Non-Final Office Action for U.S. Appl. No. 12/784,300, filed May 20, 2010, dated Sep. 24, 2013; 37 pgs.
Hyland, Gregory E.; Notice of Allowance for U.S. Appl. No. 12/784,300, filed May 20, 2010, dated Apr. 23, 2014, 20 pgs.
Hyland, Gregory E.; Supplemental Notice of Allowability for U.S. Appl. No. 12/784,300, filed May 20, 2010, dated Aug. 1, 2014, 4 pgs.
Hyland, Gregory E.; Final Office Action for U.S. Appl. No. 14/450,452, filed Aug. 4, 2014, dated Aug. 23, 2016, 41 pgs.
Hyland, Gregory E.; Non-Final Office Action for U.S. Appl. No. 14/450,452, filed Aug. 4, 2014, dated Feb. 17, 2016, 98 pgs.
Hyland, Gregory E.; Non-final Office Action for U.S. Appl. No. 14/450,452, filed Aug. 4, 2014, dated Feb. 2, 2017, 40 pgs.
Hyland, Gregory E.; Notice of Allowability for U.S. Appl. No. 14/450,452, filed Aug. 4, 2014, dated Jul. 18, 2017, 6 pgs.
Hyland, Gregory E.; Notice of Allowance for U.S. Appl. No. 14/450,452, filed Aug. 4, 2014, dated Jun. 15, 2017, 17 pgs.
Hyland, Gregory; Corrected Notice of Allowability for U.S. Appl. No. 14/450,452, filed Aug. 4, 2014, dated Mar. 26, 2017, 4 pgs.
Hyland, Gregory; Issue Notification for U.S. Appl. No. 14/450,452, filed Aug. 4, 2014, dated Oct. 4, 2017, 1 pg.
Keyghobad, Seyamak; Issue Notification for U.S. Appl. No. 10/298,300, filed Nov. 18, 2002, dated Oct. 8, 2008; 1 pg.
Keyghobad, Seyamak; Requirement for Restriction/ Election for U.S. Appl. No. 10/298,300, filed Nov. 18, 2002, dated Feb. 9, 2006; 11 pages.
Keyghobad, Seyamak; Issue Notification for U.S. Appl. No. 12/243,452, filed Oct. 1, 2008 dated Jun. 16, 2010; 1 pg.
Keyghobad, Seyamak; Issue Notification for U.S. Appl. No. 12/490,867, filed Jun. 24, 2009, dated Feb. 29, 2012; 1 pg.
Keyghobad, Seyamak; Non Final Rejection for U.S. Appl. No. 12/490,867, filed Jun. 24, 2009, dated Mar. 21, 2011; 9 pgs.
Keyghobad, Seyamak; Non Final Rejection for U.S. Appl. No. 12/490,867, filed Jun. 24, 2009, dated Oct. 4, 2010; 13 pgs.
Keyghobad, Seyamak; Notice of Allowance for U.S. Appl. No. 12/490,867, filed Jun. 24, 2006, dated Sep. 7, 2011; 6 pgs.
Keyghobad, Seyamak; Notice of Allowance for U.S. Appl. No. 12/490,867, filed Jun. 24, 2009, dated Nov. 2, 2011; 17 pgs.
Keyghobad, Seyamak; Issue Notification for U.S. Appl. No. 12/490,925, filed Jun. 24, 2009; dated Mar. 18, 2010; 1 pg.
Keyghobad, Seyamak; Non-final office action for U.S. Appl. No. 12/490,925, filed Jun. 24, 2009, dated Dec. 23, 2009; 17 pgs.
Keyghobad, Seyamak; Notice of Allowance for U.S. Appl. No. 12/490,925, filed Jun. 24, 2009, dated Aug. 2, 2010; 8 pgs.
Keyghobad, Seyamak; Issue Notification for U.S. Appl. No. 12/490,957, filed Jun. 24, 2009; dated Aug. 4, 2010; 1 pg.
Keyghobad, Seyamak; Issue Notification for U.S. Appl. No. 13/372,408, filed Feb. 13, 2012, dated Mar. 6, 2013; 1 pg.
Keyghobad, Seyamak; Non-final Office Action for U.S. Appl. No. 13/372,408, filed Feb. 23, 2012; dated May 25, 2012; 17 pgs.
Keyghobad, Seyamak; Notice of Allowance for U.S. Appl. No. 13/372,408, filed Feb. 13, 2012; dated Jul. 27, 2012; 11 pgs.
Keyghobad, Seyamak; Notice of Allowance for U.S. Appl. No. 13/372,408, filed Feb. 13, 2012; dated Nov. 1, 2012; 18 pgs.
Keyghobad, Seyamak; Supplemental Notice of Allowance for U.S. Appl. No. 13/372,408, filed Feb. 13, 2012; dated Aug. 2, 2012; 7 pgs.
Keyghobad, Seyamak, Issue Notification for U.S. Appl. No. 13/590,954, filed Aug. 21, 2012, dated Sep. 11, 2013, 1 pg.
Keyghobad, Seyamak; Non-Final Office Action for U.S. Appl. No. 13/590,954, filed Aug. 21, 2012, dated Dec. 13, 2012; 39 pgs.
Keyghobad, Seyamak; Notice of Allowance for U.S. Appl. No. 13/590,954, filed Aug. 21, 2012, dated Mar. 21, 2013, 22 pgs.
Keyghobad, Seyamak; Notice of Allowance for U.S. Appl. No. 13/590,954, filed Aug. 21, 2012, dated Jul. 9, 2013, 21 pgs.
Vonroll Hydro—Hydrojournal, pp. 1-16, May 2008.
English Translation: Vonroll Hydro—Hyrdojournal, Technology with a Future for Shut-off Systems—p. 4, VonRoll Hydro (shop) GmbH—New Concepts for Apprentice Training—p. 12, May 2008.
Von Roll Hydro—Hydrojournal, pp. 1-16, Nov. 2008.
English Translation: Von Roll Hydro—Hyrdojournal,VonRoll Hydroalert—Provides a Warning in the Event of Any Tampering with the Water Supply, p. 3, Nov. 2008.
Hyland, Gregory E.; Issue Notification for U.S. Appl. No. 14/928,725, filed Oct. 30, 2015, dated Mar. 14, 2018, 1 pg.
Hyland, Gregory E.; Supplemental Notice of Allowance for U.S. Appl. No. 14/928,725, filed Oct. 30, 2015, dated Feb. 27, 2018, 6 pgs.
Keyghobad, Seyamak; Examiner Interview Summary Record for U.S. Appl. No. 10/298,300, filed Nov. 18, 2002; dated Feb. 5, 2008; 2 pages.
Keyghobad, Seyamak; Non-Final Rejection for U.S. Appl. No. 10/298,300, filed Nov. 18, 2002; dated Oct. 26, 2007; 35 pages.
Keyghobad, Seyamak; Requirement for Restriction/ Election for U.S. Appl. No. 10/298,300, filed Nov. 18, 2002; dated Feb. 27, 2006; 17 pages.
Keyghobad, Seyamak; Certificate of Correction for U.S. Appl. No. 10/298,300, filed Nov. 18, 2002; dated Mar. 31, 2009; 1 page.
Keyghobad, Seyamak; Notice of Allowance for U.S. Appl. No. 10/298,300, filed Nov. 18, 2002; dated Jul. 14, 2008; 4 pages.
Keyghobad, Seyamak; Non-Final Rejection or U.S. Appl. No. 10/298,300, filed Nov. 18, 2002; dated Jun. 6, 2007; 32 pages.
Keyghobad, Seyamak; Non-Final Rejection for U.S. Appl. No. 10/298,300, filed Nov. 18, 2002; dated May 18, 2006; 13 pages.
Keyghobad, Seyamak; Notice of Allowance for U.S. Appl. No. 12/243,452, filed Oct. 1, 2008; dated Mar. 22, 2010; 7 pages.
Keyghobad, Seyamak; Examiner Interview Summary Record for U.S. Appl. No. 12/243,452, filed Oct. 1, 2008; dated Dec. 7, 2009; 3 pages.
Keyghobad, Seyamak; Non-Final Rejection for U.S. Appl. No. 12/243,452, filed Oct. 1, 2008; dated Sep. 14, 2009; 12 pages.
Keyghobad,Seyamak; Non-Final Rejection for U.S. Appl. No. 12/243,452, filed Oct. 1, 2008; dated May 1, 2009; 5 pages.
Keyghobad, Seyamak; Notice of Allowance for U.S. Appl. No. 12/490,925, filed Jun. 24, 2009; dated Jul. 19, 2010; 8 pages.
Keyghobad, Seyamak; Notice of Allowance for U.S. Appl. No. 12/490,925, filed Jun. 24, 2009; dated Jun. 28, 2010; 10 pgs.
Keyghobad, Seyamak; Notice of Allowance for U.S. Appl. No. 12/490,957, filed Jun. 24, 2009; dated Jun. 24, 2010; 10 pgs.
Radix Corporation; "Automatic Meter Reading", 2 pgs.
Trace; "Pit Water-Meter Transponder"; User Guide; Jan. 2003 16 pgs.
Ansi; "Protocol Specification for ANSI Type 2 Optical Port", American National Standard, ANSI C.12.18-2006, 11 pgs.
Federal Communications Commission; "Understanding the FCC Regulations for Low-Power, Non-Licensed Transmitters", Office of Engineering and Technology; Oct. 1993; 34 pgs.
Semtech; "TN1200.4, Calculating Radiated Power and Field Strength for Conducted Power Measurements", Semtech Corporation, Camarillo, CA, 2007, 9 pgs.
RFM; "HX 2000 Datasheet: 916.5 MHz: Hybrid Transmitter", RF Monolithics, Inc., Dallas, TX, USA, 1998; 2 pgs.
General Electric; "GEH-5081 kV Meter Product Manual", Nov. 1997, 137 pgs.

(56) References Cited

OTHER PUBLICATIONS

General Electric; "kV RSX—RS232/RS485 Communications Options: Instructions Manual"; Mar. 1999, 33 pgs.
Orfield; "Badger® ORION® System Helps Lemmon, South Dakota Reduce Read Time, Billing Cycles", Badger Connect Publication, 2004, 2 pgs.
AMCO; "Pit Water-Meter Transponder (PWT)"; AMCO Automated Systems, LLC; PDB-14611; Sep. 2002; 2 pgs.
AMCO; "Short-Range Programmer (SRP) VRT"; AMCO Automated Systems, LLC; PDB-14555.1; Sep. 2002; 2 pgs.
AMCO; Remote Water-Meter Transponder (RWT); AMCO Automated Systems, LLC; PDB-14610; Sep. 2002; 2 pgs.
Article entitled: "Remote Meter Reading", http://www.meter.co.uk/RMR.html; accessed on Jul. 30, 2012, 2 pgs.
Article entitled: "Datamatic, Badger Connect for AMR Solutions", http://www.datamatic.com/badger_partnership.html; accessed on Jul. 27, 2012, 1 pg.
Article entitled: "OET Exhibits List", https://apps.fcc.gov/oetcf/eas/reports/ViewExhibitReport.cfm?mode=Exhibits&RequestTimeout=500&calledFromFrame=N&application_id=194044&fcc_id=; Feb. 20, 2001, 2 pgs.
Patterson, Tim; Request for Ex Parte Reexamination under U.S. Appl. No. 90/012,468, filed Sep. 6, 2012; 52 pgs.
Patterson, Tim; Request for Ex Parte Reexamination under U.S. Appl. No. 90/012,449, filed Aug. 23, 2012; 51 pgs.
"Young et al. "Real-Time Intranet-Controlled Virtual Instrument Multiple-Circuit Power Monitoring," IEEE Transactions on Instrumentation and Measurement, Jun. 2000. vol. 49, No. 3, p. 570. [Accessed Dec. 29, 2011]http://ieeexplore.ieee.org/xpls/abs_all.jsp?".
"De Almeida et al. "Advanced Monitoring Technologies for the Evaluation of Demand-Side Management Programs," IEEE Transactions on Power Systems, Aug. 1994. vol. 9, No. 3. [Accessed Dec. 29, 2011]http://ieeexplore.ieee.org/xpls/abs_all.jsp?arnumber=336086".
"Dolezilek. "Microprocessor Based Relay Information Improves the Power System," Rural Electric Power Conference, May 1999. p. B5/1-B5/9. [Accessed Dec. 29, 2011]http://ieeexplore.ieee.org/xpls/abs_all.jsp?arnumber=768685".
Gehami et al. "Electronic Control System | Salient Feature in Substation," Transmission & Distrubition, Mar. 1991. vol. 43, No. 3, p. 48. [Accessed Dec. 29, 2011—ProQuest].
Horlent. "New Metering and Reading Techniques Based on a Modular Design Concept," 10th International Conference on Electricity Distribution, May 1989. vol. 5, p. 455-459. [Accessed Dec. 29, 2011—IEEExplore].
""In Brief," Land Mobile Radio News, Jan. 16, 1998. vol. 52, No. 3, p. 1. [Accessed Dec. 29, 2011—ProQuest] http://proquest.umi.com/pqdweb?did=25435781&sid=1&Fmt=3&clientId=31810&RQT=309&VName%20=PQD".
""Landis & Gyr Utilities: Service Partnership Helps Utilities Use Available Resources More Effectively," www.landisgyr.com/utilities/e/fr_press1_e.htm (archived Feb. 6, 1998) http://web.archive.org/web/19980206060801/http://www.landisgyr.com/utilities".
Tamarkin. "Automated Meter Reading", Sep.-Oct. 1992, vol. 50, No. 5/ [Accessed Dec. 29, 2011] http://www.usclcorp.com/news/Automatic_Power_reading.pdf.
Hyland; International Preliminary Report on Patentability for serial No. PCT/US2009/062247, filed Oct. 27, 2009, dated May 3, 2011, 7 pgs.
Hyland, Gregory E.; International Search Report for serial No. PCT/US2009/062247, filed on Oct. 27, 2009, dated Dec. 18, 2009, 2 pgs.
Hyland, Gregory E.; Canadian Office Action for Serial No. 2,741,843, filed Oct. 27, 2009, dated Apr. 25, 2017, 7 pgs.
Hyland, Gregory E.; Canadian Office Action for serial No. 2,741,843, filed Oct. 27, 2009, mailed Jul. 22, 2016, 5 pgs.
Clark, Kenneth A.; Notice of Allowance for U.S. Appl. No. 14/209,257, filed Mar. 13, 2014, dated Mar. 27, 2018, 26 pgs.
Clark, Kenneth A.; Final Office Action for U.S. Appl. No. 15/347,849, filed Nov. 10, 2016, dated Jun. 1, 2018, 29 pgs.
Clark, Kenneth A.; Examination Report for Australian application No. 2018200410, filed Mar. 13, 2014, dated Jun. 28, 2018, 4 pgs.
Wikipedia; Article entitled: "Water turbine", located at (https://en.wikipedia.org/wiki/Water_turbine), 11 pgs.
Hyland, Gregory E.; Canadian Office Action for serial No. 2,741,843, filed Oct. 27, 2009, dated Dec. 8, 2015, 5 pgs.
Hyland, Gregory; Mexico Office Action for serial No. MX/a/2011/004330, filed Apr. 25, 2011, dated Oct. 3, 2013, 6 pgs.
Hyland, Gregory; Mexico Office Action for serial No. MX/a/2011/004330, filed Apr. 25, 2011, dated Jul. 18, 2013, 6 pgs.
Hyland, Gregory;Mexico Office Action for serial No. MX/a/2011/004330, filed Apr. 25, 2011, dated Mar. 21, 2013, 7 pgs.
Hyland; European Examination Report for serial No. EP09824079.9, filed Oct. 27, 2009, dated Nov. 13, 2015; 6 pgs.
Hyland; European Search Report for serial No. EP09824079.9, filed Oct. 27, 2009, dated May 8, 2012; 38 pages.
Hyland, Gregory; Australian Patent Examination Report for serial No. 2009308949, filed Oct. 27, 2009, dated Nov. 12, 2013, 3 pgs.
Hyland, Gregory E.; Decision of Rejection for Japanese serial No. 2011-533427, filed Oct. 27, 2009, dated Sep. 16, 2014, 4 pgs.
Hyland, Gregory E.; Japanese Office Action for serial No. 2011-533427, filed Oct. 27, 2009, dated Feb. 4, 2014, 50 pgs.
Hyland, Gregory E.;Japanese Office Action for serial No. 2011-533427, filed Oct. 27, 2009, dated Apr. 30, 2013, 15 pgs.
Hyland, Gregory E.; Australian Examination Report for serial No. 2014259545, filed Oct. 27, 2009, dated Jun. 10, 2015; 2 pgs.
Hyland; International Preliminary Report on Patentability for serial No. PCT/US2010/035666, filed May 20, 2010, dated Nov. 22, 2011, 6 pgs.
Hyland; International Search Report and Written Opinion for serial No. PCT/US2010/035666, filed May 20, 2010, dated Jul. 16, 2010, 7 pgs.
Hyland, Gregory E.; Office Action for Canadian patent application No. 2,772,545, filed May 20, 2010, dated Jun. 22, 2017, 3 pgs.
Hyland, Gregory E.; Office Action for Canadian application No. 2,772,545, filed May 10, 2010, dated Jul. 27, 2016, 4 pgs.
Hyland, Gregory E.; Mexico Final Office Action for serial No. MX/a/2011/012383, filed May 20, 2010, dated Jan. 9, 2014, 9 pgs.
Hyland, Gregory E.; Mexico Office Action for serial no. MX/A/2011/012383, filed May 20, 2010, dated Sep. 3, 2013, 10 pgs.
Hyland, Gregory E.; Mexico Office Action for serial No. MX/A/2011/012383, filed May 20, 2010, dated May 9, 2013, 8 pgs.
Hyland, Gregory E.; Mexico Office Action for serial No. MX/A/2011/012383, filed May 20, 2010, dated Oct. 8, 2012, 3 pgs.
Hyland, Gregory E.; European Search Report for Serial No. EP10778423.3, filed Nov. 18, 2011, dated Apr. 10, 2017, 6 pgs.
Hyland, Gregory E.; European Search Report for serial No. EP2433440, filed Nov. 18, 2011, dated Nov. 28, 2012, 6 pgs.
Hyland, Gregory E.; Australian Patent Examination report for serial No. 2010249499, filed Nov. 17, 2011, dated Nov. 21, 2014, 5 pgs.
Hyland, Gregory E.; Australian Patent Examination report for serial No. 2010249499, filed Nov. 17, 2011, dated Jun. 16, 2014, 5 pgs.
Hyland, Gregory; Decision of Rejection for Japanese serial No. 2012-512048, filed May 20, 2010, dated Apr. 22, 2014, 10 pgs.
Hyland, Gregory; Japanese Office Action for serial No. 2012-512048, filed May 20, 2010, dated Oct. 22, 2013, 51 pgs.
Hyland, Gregory; Mexico Office Action for serial No. MX/a/2012/015236, filed Dec. 19, 2012, dated Dec. 3, 2013, by foreign associate on Jan. 9, 2014, 4 pgs.
Hyland, Gregory; Mexico Office Action for serial No. MX/a/2012/015236, filed Dec. 19, 2012, dated Oct. 3, 2013, 8 pgs.
Hyland, Gregory; Mexico Office Action for serial No. MX/a/2012/015236, filed Dec. 19, 2012, dated Jun. 13, 2013, 4 pgs.
Hyland, Gregory E.; Australian Patent Examination report for serial No. 2015202223, filed May 20, 2010, dated Nov. 4, 2015, 4 pgs.
Hyland; U.S. Provisional Patent Application entitled: Water Supply Infrastructure Monitoring System and Method, having U.S. Appl. No. 61/108,770, filed Oct. 27, 2008, 11 pgs.
Hyland; U.S. Provisional Patent Application entitled: Water Supply Infrastructure Monitoring System and Method, having U.S. Appl. No. 61/180,600, filed May 22, 2009, 14 pgs.

(56) References Cited

OTHER PUBLICATIONS

Clark, Kenneth A.; Non-Final Office Action for U.S. Appl. No. 14/209,257, filed Mar. 13, 2014, dated Oct. 16, 2017, 33 pgs.
Clark, Kenneth A.; Applicant-Initiated Interview Summary for U.S. Appl. No. 14/209,257, filed Mar. 13, 2014, dated Jul. 19, 2017, 7 pgs.
Clark, Kenneth A.; Final Office Action for U.S. Appl. No. 14/209,257, filed Mar. 13, 2014, dated Jun. 28, 2017, 41 pgs.
Clark, Kenneth A.; Non-final Office Action for U.S. Appl. No. 14/209,257, filed Mar. 13, 2014, dated Feb. 22, 2017, 95 pgs.
Clark, Kenneth A.; Restriction Requirement for U.S. Appl. No. 14/209,257, filed Mar. 13, 2014, dated Oct. 4, 2016, 7 pgs.
Clark, Kenneth A.; Non-Final Office Action for U.S. Appl. No. 15/347,849, filed Nov. 10, 2016, dated Nov. 3, 2017, 84 pgs.
Gifford, Paul; Final Office Action for U.S. Appl. No. 15/171,722, filed Jun. 2, 2016, dated Mar. 30, 2018, 15 pgs.
Gifford, Paul; Non-Final Office Action for U.S. Appl. No. 15/171,722, filed Jun. 2, 2016, dated Nov. 17, 2017, 90 pgs.
Gifford, Paul; Non-Final Office Action for U.S. Appl. No. 15/171,722, filed Jun. 2, 2016, dated Oct. 16, 2017, 76 pgs.
Clark, Kenneth A.; International Preliminary Report on Patentability for PCT/US2014/025617, filed Mar. 13, 2014, dated Sep. 24, 2015, 12 pgs.
Clark, Kenneth A.; International Search Report and Written Opinion for serial No. PCT/US2014/025617, filed Mar. 13, 2014, dated Aug. 27, 2014, 48 pgs.
Huang, et al.; "The Mahalanobis-Taguchi system—Neural network algorithm for data mining in dynamic environments", Extern Systems with Appklications (online), 2009 [retrieved on Aug. 13, 2014], vol. 36, pp. 5475-5480.
Clark, Kenneth A.; Extended European Search Report for serial No. 14771115.4, filed Mar. 13, 2014, dated Sep. 14, 2016, 8 pgs.
Stoianov, et al.; Article entitled: "Sensor Networks for Monitoring Water Supply and Sewer Systems: Lessons from Boston", Water Distribution Systems Analysis Symposium 2006; , Aug. 27-30, 2006, 17 pgs.
Perelman, et al.; Article entitled: "Event Detection in Water Distribution Systems from Multivariate Water Quality Time Series", Environmental Science & Technology, vol. 46, No. 15, Aug. 7, 2012, 8 pgs.
Palau, et al.; Article entitled: "Using Multivariate Principal Component Analysis of Injected Water Flows to Direct Anomalous Behaviors in a Water Supply System. A Case Study.", Water Science and Technology: Water Supply, vol. 4, No. 3, Jun. 30, 2004, 12 pgs.
Clark, Kenneth A.; Office Action for Mexico Application No. MX/a/2015/011793, filed Mar. 13, 2014, dated Jun. 20, 2017, 8 pgs.
Clark, Kenneth A.; Office Action for Mexico Application No. MX/a/2015/011793, filed Mar. 13, 2014, dated Feb. 20, 2017, 7 pgs.
Clark, Kenneth A.; Office Action for Australian Application No. 2014235054, filed Mar. 13, 2014, dated Jun. 2, 2017, 3 pgs.
Dukes, Brent; International Search Report and Written Opinion for application No. PCT/US15/44140, filed Aug. 7, 2015, dated Dec. 30, 2015, 15 pgs.
Gifford, Paul; Notification Concerning International Preliminary Report on Patentability for PCT Application No. PCT/US16/36007, filed Jun. 6, 2016, dated Dec. 14, 2017, 9 pgs.
Gifford, Paul; International Search Report and Written Opinion for PCT Application No. PCT/US16/36007, filed Mar. 6, 2016, dated Oct. 6, 2016, 12 pgs.
Clark, Kenneth A.; U.S. Provisional Patent Application entitled: Systems for Measuring Properties of Water in a Water Distribution System , U.S. Appl. No. 61/794,616, filed Mar. 15, 2013; 49 pgs.
Gifford, Paul; U.S. Provisional Patent Application entitled: Distribution System Monitoring having U.S. Appl. No. 62/171,897, filed Jun. 5, 2015, 42 pgs.
Hyland, Gregory E.; Extended European Search Report for serial No. 18184468.9, filed May 20, 2010, dated Dec. 3, 2018, 9 pgs.
Hyland, Gregory E.; Extended European Search Report for serial No. 18184481.2, filed May 20, 2010, dated Dec. 3, 2018, 9 pgs.
Hyland, Gregory E.; Office Action for Canadian patent application No. 2,997,878, filed Oct. 27, 2009, dated Dec. 10, 2018, 4 pgs.
Icelandic Building Research Institute, et al.; "Monitoring corrosion in district heating systems", Nordic Innovation, Project No. 00071, Final Report, pp. 1-254, May 2004 (May 2004).
Clark, Kenneth A.; Issue Notification for U.S. Appl. No. 14/209,257, filed Mar. 13, 2014, dated Dec. 22, 2018, 1 pg.
Clark, Kenneth A.; Issue Notification for U.S. Appl. No. 15/347,849, filed Nov. 10, 2016, dated Jan. 23, 2019, 1 pg.
Gifford, Paul; Final Office Action for U.S. Appl. No. 15/171,722, filed Jun. 2, 2016, dated Feb. 26, 2019, 18 pgs.

\* cited by examiner

METHOD OF DISSEMINATING MONITORING INFORMATION RELATING TO CONTAMINATION AND CORROSION WITHIN AN INFRASTRUCTURE

CROSS-REFERENCE TO RELATED APPLICATIONS

This application is a continuation of U.S. patent application Ser. No. 14/928,725, filed on Oct. 30, 2015, which is a continuation of U.S. patent application Ser. No. 12/606,957 filed on Oct. 27, 2009, now U.S. Pat. No. 9,202,362, which claims the benefit of U.S. Provisional Application No. 61/108,770, filed Oct. 27, 2008, and of U.S. Provisional Application No. 61/180,600 filed May 22, 2009, the entire disclosures of which are hereby specifically and entirely incorporated by reference.

BACKGROUND

1. Field of the Invention

The invention is directed systems and methods of monitoring and controlling an infrastructure such as, but not limited to the supply and use of commercial, industrial or residential water, gas and/or electric, and, in particular, to methods and systems for monitoring and controlling a municipality and alerting a user to potential faults.

2. Background of the Invention

Municipalities administer and/or outsource numerous safety systems within each municipality. Such systems are usually complex infrastructures and include but are not limited to water distribution, gas distribution, electricity distribution, waste management, traffic control, fire departments, police departments, and emergency response departments. Each of these systems needs to be monitored for use (authorized or unauthorized), faults, tampering, events, leaks, contamination, and/or other issues.

Often to obtain an understanding of the state of any one system, or for billing or repair purposes, personnel must be sent into the municipality to manually check for problems within the system. This is slow, labor-intensive process can lead to overlooked problems. Furthermore, preferred aspects of the system may only be evaluated irregularly or infrequently, thereby allowing a problem to go unchecked for long periods of time. For example, a leak in a water main may cost a water company a significant amount of money in lost water, energy usage, and chemical treatment, particularly if the leak is not discovered for a long period of time. Furthermore, a leak can lead to underground structural erosion.

Another problem and disadvantage associated with current systems is the lack of property rights sufficient to maintain a network of monitors and device controllers capable of creating a transmission infrastructure that can adapt to multiple monitors and controllers and form an information network for providing information about the system to the utility monitoring the network. For example, some networks require new polls or towers to be erected for placement of the communication devices.

Furthermore, an issue in one system may cause an issue in another system. For example, a fire reported to the fire department may require the gas company to shut off gas flow to the vicinity of the fire and require the water company to redirect water or additional water pressure to the vicinity. However, current systems are not interoperable. Therefore, it is desirable to have a single system that can monitor different aspects of at least one municipality system continuously and communicate with several entities at the same time.

SUMMARY

The present invention overcomes the problems and disadvantages associated with current strategies and systems and provides new systems and methods of monitoring municipality infrastructure.

One embodiment of the invention is directed to a method of disseminating information. The method includes the steps of detecting, by a first monitoring device, a first condition of a first aspect of an infrastructure and transmitting a data signal to an operations center, the data signal including data relating to the first condition and a first time stamp; detecting, by a second monitoring device, the first condition of the first aspect and a second condition of a second aspect of the infrastructure, and transmitting a data signal to the operations center, the data signal including data relating to the second condition and data relating to the first condition, and the data signal comprising a second time stamp; determining, by the operations center, whether the data included in the data signal received from either of the monitoring devices indicates a problem of contamination within the infrastructure; subsequent to the determination of the indication of the problem of contamination, determining, by the operations center, an amount of the contamination, an approximate location of the contamination, a direction of contamination movement, and a speed of the contamination movement, wherein the direction and the speed of the contamination movement are based on the first time stamp from the first monitoring device and the second time stamp from the second monitoring device; determining, by the operations center, whether the data included within the data signal received from either of the monitoring devices indicates a problem of corrosion within the infrastructure; and subsequent to determination of the indication of the problem of corrosion, determining by the operations center an amount of corrosion determined to be the problem within the infrastructure and a level of severity of the corrosion. The first aspect and the second aspect define different aspects of the infrastructure.

Another embodiment is also directed to a method of disseminating information. The method includes the steps of detecting, by a first monitoring device, a condition of an aspect of an infrastructure; transmitting, by the first monitoring device, a data signal including data relating to the condition and a first time stamp; detecting, by a second monitoring device, the condition of the aspect of the infrastructure; transmitting, by the second monitoring device, a data signal including data relating to the condition and a second time stamp; determining whether the data from the first monitoring device differs from the data from the second monitoring device; determining whether a difference in data indicates a problem of contamination within the infrastructure; subsequent to the determination of the indication of the problem of contamination, determining an amount of the contamination, an approximate location of the contamination, a direction of contamination movement, and a speed of the contamination movement, wherein the direction and the speed of the contamination movement are based on the first time stamp from the first monitoring device and the second time stamp from the second monitoring device; determining, by the operations center, whether a difference in data indicates a problem of corrosion within the infrastructure; and subsequent to the determination of the indication of corrosion, determining whether the data relating to the condition as detected by the first monitoring device and the second monitoring device indicates an amount of corrosion determined to be the problem within the infrastructure, and a level of severity of the corrosion.

Other embodiments and advantages are set forth in part in the description, which follows, and in part, may be obvious from this description, or may be learned from the practice of the invention.

DESCRIPTION OF THE DRAWINGS

The invention is described in greater detail by way of example only and with reference to the attached drawings, in which.

DETAILED DESCRIPTION

Figure 1:
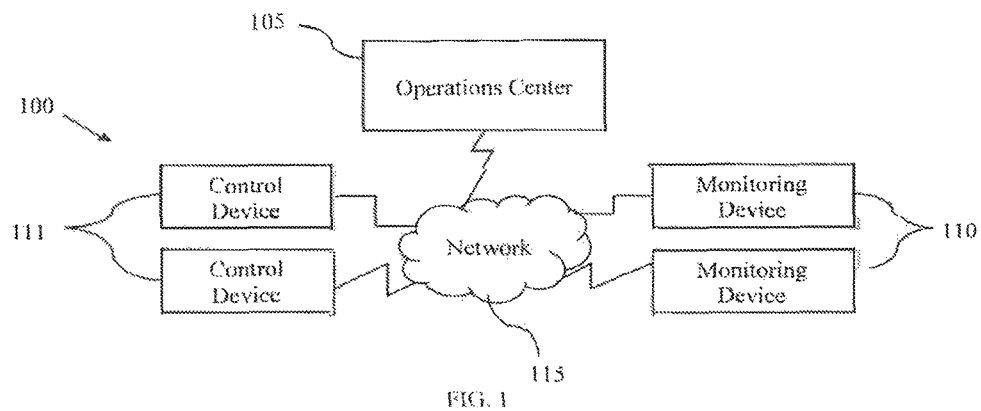
FIG. 1 is a schematic of one embodiment of the system of the invention.

As embodied and broadly described herein, the disclosures herein provide detailed embodiments of the invention. However, the disclosed embodiments are merely exemplary of the invention that may be embodied in various and alternative forms. Therefore, there is no intent that specific structural and functional details should be limiting, but rather the intention is that they provide a basis for the claims and as a representative basis for teaching one skilled in the art to variously employ the present invention.

A problem in the art capable of being solved by the embodiments of the present invention is monitoring and maintaining an infrastructure. It has surprisingly been discovered that monitoring devices with one or two way communication abilities can be used to detect faults in the municipality's systems and provide on-demand, real time, or near real time device status, maintenance, and control over the systems.

A network of monitoring devices of the invention is capable of providing a system administrator with a full picture of the current state of the system. The network preferably includes an array of different monitoring devices each capable of sensing at least one condition. The monitoring devices may be capable of sending and receiving data to and from at least one operations center. Communication may be from the remote monitoring device to a central monitoring facility, to one of a number of regional monitoring centers, to a user, and/or to a research facility. Furthermore, the system preferably includes at least one control device. Each control device is adapted to control a different aspect of the system. The control devices may be part of the monitoring devices or may be separate units. Communication is preferably over the Internet, but may be over a private network, a local area network, or a wide area network. Preferably the communication involves a wireless component, such as from the remote monitoring device and/or control device to a regional monitoring facility, or to distributed monitors. Also preferably, the communications are secured or encrypted such that the communications system cannot be monitored by another unknown party. Preferably access to the system is granted through user names and passwords, although additional and/or alternate encryption methods can be employed.

One embodiment of the invention is directed to water infrastructure systems. In such systems, monitoring devices can be located throughout the system, for example, as attachments to component parts, for feedback to a network that can provide real-time information to the utility operating the network. The network operators can use the information transmitted to activate controlling devices on the network, or to dispatch repair or other services as directed by the information provided by the network. For example, if water pressure monitors on a water meter indicate a variance between locations, a water leak can be reported using the network, and controlling devices can divert water. Pressure meters can be attached to fire hydrants to monitor and report pressure losses throughout the system, providing real-time information to benefit the users of the fire hydrants (fire departments who need to be assured of adequate pressure), the users of the system (water consumers who will be affected by lower pressure), and the operators of the system (who suffer asset loss as a result, of lack of real-time information about losses).

FIG. 1 depicts a system 100 of the invention for monitoring, controlling, and communicating with at least one monitoring device and/or at least one control device. System 100 includes an operations center 105 in communication with at least one monitoring device 110 and/or one control device 111. In the preferred embodiment, there is bi-directional communication between operations center 105 and devices 110 and 111. Communications can be simplex or duplex. Communication can occur over any communications network 115 known in the art, including but not limited to wired networks, wireless networks, Zigbee networks, Bluetooth networks, Z-wave networks, WiFi networks, WiMax networks, RF networks, local area networks (LAN), internet networks, wide area networks (WAN), cellular telephone network, hardwired telephone networks, 900 MHz wireless networks, and satellite networks. In the preferred embodiment, the network is a fixed network. For example, the fixed network can be a mesh network or a star network. Additionally, devices 110 and 111 and operations center 105 can be in direct communication or can communicate through an intermediary device, such as a relay or a gateway.

Each monitoring device 110 of the invention preferably monitors at least one aspect of the infrastructure. The monitored aspect can be one or more of the components of the infrastructure (e.g. pipe conditions, valve conditions, fire hydrant conditions, service line conditions, meter conditions, power line conditions, and battery conditions), commodity conditions (e.g. fluid or gas flow, fluid or gas pressure, fluid or gas temperature, and fluid or gas contaminants), or combinations thereof. Additionally, the monitors can be self monitoring. For example the monitors preferably determine if there is a loss of communication, low battery levels, and/or internal damage (e.g. short circuits due to water damage). Additionally, each monitoring device 110 can be structurally stable (e.g. fixed to a valve, pipe, or meter) or movable (e.g. allowed to move with or within the flow of water or gas in the pipes).

Each node in the network of the invention preferably detects errors in transmissions. Error detection can use cyclic redundancy codes using a tabled based on a defined polynomial or any other method of error detection. In preferred embodiments, transmissions can be rerouted if the primary route is blocked or otherwise unavailable. Furthermore, devices 110 and 111 can confirm receipt of a message, e.g. via a hand shake protocol. In instances where confirmation is not received the message can be resent along the same rout or rerouted.

In preferred embodiments, each monitoring device 110 and each control device 111 is assigned a unique identifier. The unique identifier can be related to the devices' geographical locations, street addresses, order of installation, or any other method of identifying the devices. Furthermore, different types of devices 110 and 111 can have identifiers that are unique to that type of device. For example, the identifier for all water meters can start with a WM, while the identifier for all leak detectors can start with a LD. Each communication to and from a device 110 and 111 can include the unique identifier so that the message is received by the correct device 110 or 111, or operations center 105 can determine where the message was sent from.

Each monitoring device 110 and each control device 111 can be retrofitted to an existing system or device, can be coupled to a new system or device, or can be integrated into a new system or device. For example, the system can be connected to, work with, or work independently of a Supervisory control and data acquisition (SCADA) network. In preferred embodiments, each monitoring device 110 and each control device 111 has a set of adapters to facilitate coupling the monitoring device 110 or control device 111 to a new or existing system or device.

In preferred embodiments, system 100 is divided into sectors with each sector having at least one monitoring device 110 and/or at least one control device 111. Each sector can communicate directly with operations center 105 or each sector can have at least one intermediary communications device that is in communication with the monitoring device 110 and/or control device 111 and operations center 105. In the preferred embodiment, the sectors are divided up by geographical location. For example, all of the devices in one neighborhood can be in a single sector and there is one sector for each neighborhood. In preferred embodiments, one intermediary communications device can service multiple sectors.

In preferred embodiments, each monitoring device 110 and/or control device 111 can communicate with adjacent monitoring devices 110 and/or control devices 111. In such embodiments, each device 110 and/or 111 can act as a transceiver or relay by receiving messages intended for another device or for the operations center 105 and forwarding the message. In embodiments where the system 100 is divided into sectors, monitoring devices 110 and control devices 111 can only communicate within their sector. In other embodiments, monitoring device 110 and control device 111 can communicate with devices 110 and/or 111 in other sectors. Each remote monitoring device 110 and/or the operations center 105 may be able to determine if a transmitted message was received by the intended device and, if not, may be able to reroute the message until the message is properly received. Additionally, relay devices can be implemented in the system to further extend the range of communications. For example, relay devices can be placed on telephone poles, on municipal buildings, within fire hydrants, and/or under manhole covers. In preferred embodiments, devices 110 and 111 communicate over a mesh network. In the mesh network, devices 110 and 111 can communicate with other devices 110 and 111 within the mesh network. Operations center 105 can set specified communications pathways derived from routing tables.

Operations center 105 can be located at a municipality office, a private or public company, a fire station, a police station, or any other entity that monitors operations center 105. In other embodiments, operations center 105 can be a remotely hosted operations center accessible by a device capable of accessing the Internet. In such embodiments, operations center 105 can take advantage of cloud computing (e.g. a network of remotely hosted computers, servers, and data storage devices). Compared to non-remotely hosted computer networks, cloud computing can increase ease of use, increase access, increase security, decrease costs, be custom tailored, and provide an unrestricted expansion of storage space. Additionally, in preferred embodiments, there is a plurality of operations centers 105. One or more operations centers can be located at different entities and each control center can monitor a different aspect of system 100. For example, in embodiments where one monitoring device monitors water usage and another monitors gas leaks, the water usage aspect can be monitored by a water utility company and the gas leaks can be monitored by the gas utility company and/or the fire department. In preferred embodiments, there are redundant operations centers 105, where at least two operations centers 105 monitor the same aspect of system 100. Operations center 105, in preferred embodiments, can send transmissions to update the firmware of devices 110 and 111.

Figure 2:
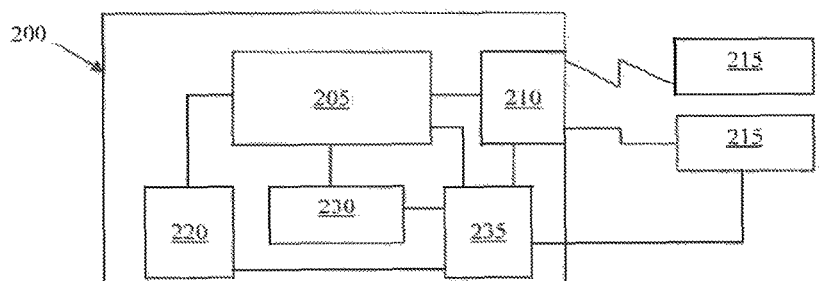
FIG. 2 is a schematic of one embodiment of the monitoring device of the invention.

FIG. 2 is a schematic of a monitoring device unit 200. Monitoring device unit 200 includes a processor 205. Processor 205 is coupled to at least one input port 210 for receiving data from sensors 215. Processor 205 is also coupled to a transceiver 220 for sending and receiving signals. In preferred embodiments, processor 205 is coupled to a data storage unit 230. Data storage unit 230 can hold a predetermined amount of data received from the sensors 215. For example, data storage unit 230 can hold data for a predetermined amount of time (e.g. one day, one week, or one month), can hold a predetermined number of readings (e.g. 10 readings, 100 readings, 1000 readings), or can hold data until directed to purge the data by the operations center. Additionally, data storage unit 230 can hold instructions for processor 205 to execute upon prompting from the operations center. In the preferred embodiments, processor 205 compiles at least some of the data stored in data storage unit 230 for transmitting to the operations center.

Each remote monitoring device 200 may collect data and/or transmit data continuously, at specific intervals, or randomly. In embodiments where the monitoring device 200 collects and transmits data in a non-continuous configuration, monitoring device 200 may turn off or reduce power consumption during the non-data collecting periods to save energy. In preferred embodiments, processor 205 is coupled to a power source 235. Power source 235 can be a device capable of powering processor 205 and devices attached to processor 205. For example, power source 235 can be a battery, solar panel array, wind turbine, water turbine, electrical lines, or combinations thereof. In preferred embodiments, there is also a backup power source, such as a battery. In preferred embodiments, the power may derive from the operation of the infrastructure system.

In the preferred embodiment, processor 205 is coupled to at least one sensor 215 that monitors at least one condition associated with the monitoring device. In preferred embodiments, sensors 215 can determine the status of a device. Sensors 215 can be directly wired to processor 205 or can use wireless communication to send and receive signals from processor 205. Sensors 215 can be positioned within the monitoring device or be external to the monitoring device. In preferred embodiments, sensors 215 are positioned remote from the monitoring device. For example a sensor can be positioned on a nearby building or telephone pole. In the embodiments, where sensors 215 and processor 205 communicate wirelessly, the same communications protocol can be used in the sensor/processor communication as in the processor/operations center communication, or different communications protocols can be used in the sensor/processor communication as in the processor/control center communication. For example, the sensor/processor communications can use RF protocols while the processor/control center communications can be over a wired network.

In preferred embodiments, sensor 215 is a use monitor. In such embodiments, the use monitor records the amount of water, gas, electricity, or other commodity that is used by a customer over a specified period of time. The use monitor can continuously record the amount of the commodity used or the use monitor can provide a signal to processor 205 that the commodity is in use. Processor 205 can transmit a signal to the operations control to alert the operations center that the monitoring device is being used and/or how much of the commodity is flowing through the sensor. In preferred embodiments, the operations center can request a reading from the use monitor on demand. In preferred embodiments, the processor or the operations center can determine based on the use, if there is unauthorized use of the commodity. Upon detection of unauthorized use, at least one of processor 205 or the operations center can generate an alarm that there is unauthorized use. For example, in embodiments where the use monitor is coupled to a fire hydrant, if the use monitor indicates that the fire hydrant is in use, however no fire is reported, the operations center can disseminate an alert that there is potential misuse of the fire hydrant.

In preferred embodiments, at least one sensor 215 is a tamper sensor. The tamper sensor can be a motion detector, a contact sensor, a rotation sensor, a touch sensor, a proximity sensor, a biofeedback sensor, a temperature sensor, a capacitance sensor, a resistance sensor, or any other sensor that is able to detect the presence of an object. The tamper sensor can send a message to processor 205 when the tamper sensor detects an event. The processor 205 will then evaluate the event to determine if a device being monitored is being tampered with or will relay the message to the operations center for evaluation. The monitored device can be a fire hydrant, utility meter, valve, manhole cover, pump, or any other device that may be tampered with. Upon detection of a tamper event, at least one of processor 205 and the operations center can generate an alarm that the device is being tampered with. In preferred embodiments, the monitoring device may activate a tamper prevention device (described below). In preferred embodiments, the operations center will send a transmission to processor 205 telling processor 205 to disregard messages from the tamper sensor for a predetermined period of time or until another message is received from the operations center telling processor 205 to resume monitoring for tamper events. For example, if a fire department needs to use a fire hydrant, the operations center will send a message to processor 205 to temporarily disregard any tamper events. Once the fire department is finished using the fire hydrant the operations center will send a message to processor 205 to start monitoring for tamper events again.

In preferred embodiments at least two of sensors 215 are leak detectors. Each leak detector can include an in-pipe leak detector and/or an exterior leak detector. In gas applications, the leak detectors are preferably vapor sensors. While in liquid applications, preferably the leak detectors use acoustic monitoring to determine presence and location of a leak. The energy generated from a leak is transmitted within a pipe through the commodity as well as through the pipe wall. Each leak detector can detect the vibrations made by the leak in the commodity or the pipe wall, joint or service line. To determine the location of a leak, at least two detectors must detect the same leak. Based on the velocity of the sound traveling along the pipe (V), the distance between the two detectors (D) and the delay between the times each detector detects the sound (T), the location of the leak (L) can be determined by the following equation:

$$L=(D-(V \times T))/2$$

When using the above equation, the typical velocity of sound in water is about 1500 m/s while the typical speed of sound through an iron pipe is 5100 m/s. The velocity can be measured empirically. For example, if the leak is exactly midway between the two detectors the sound would reach both detectors at the same time. Each detector may monitor continuously or at predetermined periods of time. The leak detectors can send a message to processor 205 when the leak detectors detect an event. The processor 205 can then evaluate the event to determine if there is a leak and how severe the leak is or can relay the message to the operations center for evaluation. Upon detection of a leak event, at least one of processor 205 or the operations center can generate an alert that there is a leak if the leak is determined to be severe enough to warrant attention.

In preferred embodiments, at least one sensor 215 is a smoke detector. The smoke detector can be a photoelectric detector, an ionization detector, or any other device that can detect the presence of smoke. The smoke detector can be located within the monitoring device or exterior to the monitoring device. In the preferred embodiment, the smoke detector monitors continuously for smoke. The smoke detector can send a message to processor 205 when the smoke detector detects an event. The processor 205 can then evaluate the event to determine if there is smoke or can relay the message to the operations center for evaluation. Upon detection of smoke, at least one of processor 205 or the operations center can generate an alert that there is smoke.

In preferred embodiments, at least one sensor 215 is a temperature sensor. The temperature sensor can be a contact sensor (e.g. thermocouples, thermistors, liquid-in-glass thermometers, resistance temperature detectors, filled system thermometers, bimetallic thermometers, semiconductor temperature sensors, and phase change indicators) or a non-contact sensor (e.g. radiation thermometers, thermal imagers, ratio thermometers, optical pyrometers, and fiber optic thermometers). The temperature sensor can be located within the monitoring device or exterior to the monitoring device. In the preferred embodiment, the temperature sensor monitors continuously for the temperature to rise above or drop below a predetermined threshold. The temperature sensor can send a message to processor 205 when the temperature sensor detects a temperature beyond the thresholds. The processor 205 can then evaluate the event to determine if there the temperature is a problem (such as freezing pipes or fire) or can relay the message to the operations center for evaluation. Upon detection of undesirable temperatures, at least one of processor 205 or the operations center can generate an alert that there is an undesirable temperature condition.

In preferred embodiments, at least one sensor 215 is a rust and/or corrosion sensor. The sensor can detect rust and/or corrosion using any method known in the art, including but not limited to liquid penetration inspection, magnetic particle inspection, radiographic inspection, visual inspection, eddy current inspection, ultrasonic inspection, and thermographic inspection. The sensor can send a message to processor 205 when the sensor detects a rust or corrosion beyond a threshold value. The processor 205 can then evaluate the rust or corrosion to determine if there is a problem or can relay the message to the operations center for evaluation. Upon detection of undesirable rust or corrosion, at least one of processor 205 or the operations center can generate an alert that there is an undesirable amount of rust or corrosion.

In preferred embodiments, at least one sensor 215 is a fluid flow sensor. Fluid flow sensor can be used either in gas systems or liquid systems. The fluid flow sensor can detect direction of the flow, turbidity of the flow, velocity of the flow, density of the flow, viscosity of the flow, and/or any other aspect of the flow. The fluid flow sensor may be a velocimeter, a laser-based interferometer, a vane, a rotary potentiometer, a Hall effect sensor, a device to measure heat transfer caused by the flowing fluid, or any other device know in the art to measure the flow of fluid. The sensor can send a message to processor 205 when the sensor detects a flow anomaly. The processor 205 can then evaluate the event to determine if the anomaly is a problem or can relay the message to the operations center for evaluation. Upon detection of an anomaly, at least one of processor 205 and the operations center can generate an alert that there is an anomaly.

In preferred embodiments, at least one sensor 215 is a pressure sensor. In the preferred embodiment, the pressure sensor is positioned within the flow of fluid or area in which the pressure is being sensed. For example, the pressure sensor can be positioned at the base of a fire hydrant and in the water to determine the water pressure within water system, in a pipe to determine gas or water pressure within a gas or water system, or in a room to determine air pressure within the room. The pressure sensor can be a piezoresistive strain gauge, a capacitive gauge, an electromagnetic gauge, a piezoelectric device, or any other device know in the art to measure pressure. The sensor can send a message to processor 205 when the sensor detects a pressure anomaly. The processor 205 can then evaluate the event to determine if the anomaly is a problem or can relay the message to the operations center for evaluation. Upon detection of an anomaly, at least one of processor 205 or the operations center can generate an alert that there is an anomaly.

In preferred embodiments, at least one sensor 215 is a water quality monitor. The water quality monitor can monitor a single aspect of water flowing through the system or multiple aspects of the water. For example, the water quality monitor can monitor one or more of the water's bacteria levels, pharmaceutical levels, alkalinity, chlorine and/or chloramine levels, hardness, pH levels, peroxide content, iron levels, nitrate levels, nitrite levels, arsenic levels, pollution levels, oxygen levels, biomass levels, and/or any of the other contaminants regulated by the Environmental Protection Agency (EPA), in embodiments where there are multiple monitoring devices, all the devices can monitor the same aspects, each device can monitor a different aspect, or a combination thereof. In the preferred embodiment, the water quality monitors test the water continuously, however, in preferred embodiments, the water quality monitors test the water at predetermined time intervals (e.g. once, a hour, once a day, once a week, etc.). Each water qualify monitor relays data to processor 205. Processor 205 can store the data on database 230 or transmit the data to the operations center. Either processor 205 or the operations center can monitor the data received from the water quality monitors to determine if there is a change in the levels of the contaminants or if the levels of the contaminants rise above a threshold, level. Upon detection of unsafe contamination levels, at least one of processor 205 or the operations center can generate an alert that there is contamination in the water system.

In the embodiments where at least two monitoring devices are monitoring the same aspect of the water, the operations center can determine if there is a change in the aspect of the water from the location of one monitoring device to the location of the other. If there is a change, the operations center can generate an alert that there is a change in the water system and output the approximate location of the change in the aspect of the water.

In preferred embodiments, at least one sensor 215 is an air quality monitor. The air quality monitor can monitor a single aspect of the air or multiple aspects of the air. Furthermore, the air quality monitor can monitor the air within a facility or ambient air. For example, the air quality monitor can monitor one or more of the air's benzene levels, carbon disulfide levels, urethane levels, formaldehyde levels, phosphorus levels, naphthalene levels, parathion levels, quinoline levels, trifluxalin levels, and/or any of the other contaminants whose acceptable levels have been set by the Environmental Protection Agency. In embodiments were there are multiple monitoring devices, all the devices can monitor the same aspects or each device can monitor a different aspect, or a combination thereof. In the preferred embodiment, the air quality monitors test the air continuously, however, in preferred embodiments, the air quality monitors test the air at predetermined time intervals (e.g. once a hour, once a day, once a week, etc.). Each air quality monitor relays data to processor 205. Processor 205 can store the data on database 230 or transmit the data to the operations center. Either processor 205 or the operations center can monitor the data received from the air quality monitors to determine if there is a change in the levels of the contaminants or if the levels of the contaminants rise above a threshold level. Upon detection of unsafe contamination levels, at least one of processor 205 or the operations center can generate an alert that there is contamination in the air.

In the embodiments where at least two monitoring devices are monitoring the same aspect of the air, the operations center can determine if there is a change in the aspect of the air from the location of one monitoring device to the location of the other. If there is a change, the operations center can generate an alert that there is a change in the air and output the approximate location of the change in the aspect of the air. Furthermore, in embodiments where there is a time stamp associated with each reading, the control center can determine the approximate direction and speed at which the contaminant is moving.

In preferred embodiments, at least one sensor 215 is a motion detector. The motion detector can be a radar-based motion detector, a photo-sensor motion detector, a passive infrared motion detector, a magnetic motion detector, a pressure sensitive motion detector, or any other device capable of detection the motion of objects. The motion detector can be used, for example, to count the number of cars passing through an intersection to control a traffic light, for tamper prevention as described above, for security purposes, and/or to control street lights. The motion detector can be placed within the monitoring device or exterior to the monitoring device. Upon detecting motion, the motion detector can relay the detection to processor 205. Processor 205 can save the detection on database 230 or transmit a message regarding the detection to the operations center. Processor 205 or the operations center can evaluative the detection and act in accordance with the purpose of the motion detector. For example, if the motion detector detects a predetermined number of vehicles have passed the monitoring device, processor 205 or the operations center can cause a traffic light to switch from green to red. As a second example, if the motion detector detects a motion after a predetermined time, e.g. after sunset, processor 205 or the operations center can cause the street lights near the monitoring device to illuminate for a predetermined period of time.

In preferred embodiments, at least one sensor 215 is a tiltmeter. The tiltmeter can be a pendulum, a water tube, a bubble-level meter, and/or a MEMS electronic meter. The tiltmeter can be located on devices within the system, such as, but not limited to, pipes, fire hydrants, meters, valves, telephone poles, manhole covers, and light posts. The sensor can send a message to processor 205 when the sensor detects a tilt beyond a threshold value. The processor 205 can then evaluate the tilt to determine if there is a problem or can relay the message to the operations center for evaluation. Upon detection of undesirable tilt, at least one of processor 205 or the operations center can generate an alert that there is an undesirable tilt. For example, if a telephone pole is struck by a car, the tiltmeter will indicate that the telephone pole is tilting at an undesirable level and the operations center can alert the municipality to send out a repair crew to assess the situation and repair the telephone pole.

In preferred embodiments, at least one sensor 215 is a proximity sensor. The proximity sensor can use electromagnetic technology, electrostatic technology, infrared technology, or a touch switch. The proximity sensor can detect if devices are properly closed or if devices are improperly touching. The sensor can send a message to processor 205 when the sensor detects proximity beyond a threshold value. The processor 205 can then evaluate the proximity to determine if there is a problem or can relay the message to the operations center for evaluation. Upon detection of undesirable proximity, at least one of processor 205 or the operations center can generate an alert that there is an undesirable proximity. For example, if a valve is improperly closed, the proximity sensor will indicate that the valve is not closed and processor 205 can alert the municipality to take proper actions to close the valve.

In preferred embodiments, at least one sensor 215 is a camera. The camera can be an infrared camera, a video camera, a still camera, a digital camera, a film camera, combinations thereof, or any other device capable of acquiring an image. In a preferred embodiment, the camera is a digital video camera that takes video images continuously. In another preferred embodiment, the camera is a digital still camera that takes still images at regular intervals or upon command from processor 205. In preferred embodiments, the camera can be a traffic camera and take a picture when instructed to by processor 205, for example upon determination that a vehicle is running a red light. In other embodiments, the camera is be use to perform visual inspections of the systems infrastructure. For example, the field of view of the camera can include a device within the system that is apt to corrode and the camera can provide an easy method to visually inspect any degradation of the device. The camera can send image data to processor 205 where the data is stored on database 230 or is transmitted to the operations center. In preferred embodiments, image data is streamed continuously from the camera to processor 205 and from processor 205 to the operations center. The data stream can either be live or delayed. The camera can be located on the monitoring device, near the monitoring device, or within the monitoring device with a portion of the camera extending outside the monitoring device or with a hole in the monitoring device through which the camera can obtain images. In preferred embodiments, the camera is positioned on an actuator. The actuator can move to reposition the field of view of the camera. The actuator can move upon demand from processor 205 or can move autonomously. In the embodiments where the actuator moves autonomously, the movement can be continuous or sporadic.

In preferred embodiments, at least one sensor 215 is a Global Positioning System (GPS) receiver. In the preferred embodiment, the GPS receiver is located on devices within the system, such as, but not limited to, pipes, fire hydrants, meters, valves, telephone poles, manhole covers, and light posts. The sensor can send a message to processor 205 indicating the sensor location. The processor 205 can then relay the message to the operations center for evaluation, conformation, and documenting. Upon detection of unexpected location, at least one of processor 205 or the operations center can generate an alert mat the sensor has moved, possibly indicating that the device has been dislodged, tampered with, or stolen. Additionally, the GPS location can be used, for example, by emergency responders to locate fire hydrants, or repair crews to determine the location of a buried device. In such embodiments, the operations center can disseminate information to the emergency responders or repair crews to easily locate the device. The dissemination can occur by any method, including but not limited to, verbally, over a telecommunications network (e.g. to a smart phone or portable computer), or over a shortwave radio. In embodiments where the monitoring device is moving with the flow of fluid, the sensor can provide updated locations of the monitoring device to track, for example, the flow or contamination levels within the flow.

Other possible sensors 215 connected to monitoring device 200 can include, but are not limited to, flow rate meters, backflow meters, system status monitors, and power level monitors.

Figure 3:
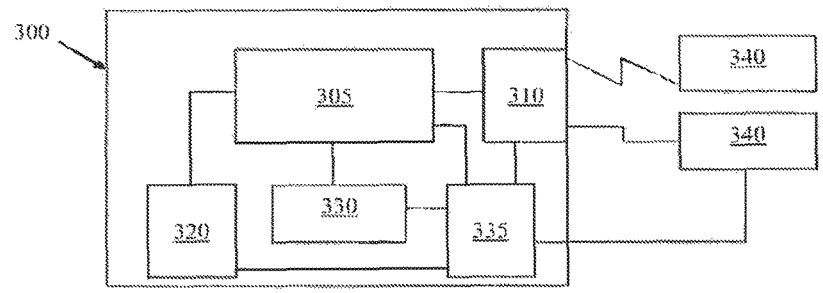
FIG. 3 is a schematic of one embodiment of a control device of the invention.

FIG. 3 is a schematic of a control device 300. Control device 300 includes a processor 305. Processor 305 is coupled to at least one output port 310 for controlling an output device 340. Processor 305 is also coupled to a transceiver 320 for sending and receiving signals. Processor 305 is communicatively coupled to output port 310. Output port 310 is connected to at least one output device 340. Each output device can 340 have the same purpose or each output device 340 can have a different purpose, or combinations thereof. Output devices 340 can be located within control device 300 or external to control device 300, as shown. Furthermore, output devices 340 can be attached to control device 300 or can be remote from control device 300. Output devices 340 communicate with output port 310 through wired or wireless communication channels. In preferred embodiments, output devices 340 are capable of bidirectional communication. In preferred embodiments, control device 300 is an integral part of a monitoring device. In such embodiments, the control device and the monitoring device can share the same processor and/or transceiver.

In preferred embodiments, processor 305 is coupled to a data storage unit 330. Data storage unit 330 may store instructions for processor 305 of how to control output devices 340. In preferred embodiments, processor 305 is coupled to a power source 335. Power source 335 can be any device capable of powering processor 305 and any devices attached to processor 305. For example, power source 335 can be a battery, solar panel array, wind turbine, water turbine, electrical lines, or combinations thereof. In preferred embodiments, there is also a backup power source, such as a battery.

In preferred embodiments, at least one output device 340 is an actuator control device. The actuator control device can control any type of actuator, including but not limited to, a tamper prevention device, a locking device, a camera motion device, a fire hydrant nut opening device, or a valve. The actuator control device can control the actuator autonomously or upon demand from processor 305. For example, upon receiving a signal that a particular event has been sensed, processor 305 may send a command to the actuator control device to act in a particular manner. Likewise, in preferred embodiments the control signal may come from the operations center. The actuator can be mechanical, electrical, or a combination thereof.

In preferred embodiments, at least one output device 340 is an alarm. The alarm can be a visual alarm, an audible alarm, a tactile (i.e. vibration) alarm, or a combination thereof. The alarm can be located within the monitoring device, exterior to the monitoring device, at the operations center, remote from the system, or any other location to alert people. Furthermore, there can be more than one alarm at different locations. For example, in the embodiments where there is a smoke detector, there can be an audible alarm located within the fire detector to alert people around the monitoring device of a potential fire, there can be an audible alarm at the fire station to alert the fire department of the potential fire, and there can be a visual alarm at the gas utility company to indicate that the flow gas in the vicinity of the potential fire should be shut off. In preferred embodiments the alarm is controlled by the processor 305, while in other embodiments the alarm is controlled by the operations center. In preferred embodiments, the alarm has an on/off switch controllable locally.

In preferred embodiments, at least one output device 340 is a tamper prevention device. The tamper prevention device can be a mechanical lock, an alarm, a light, an electrical shock generator, a retaining device, an electrical lock, or any other device capable of preventing tampering. The tamper prevention device may merely deter tampering or may incapacitate a person who is trying to tamper with the device, depending on the level of security. In preferred embodiments the tamper prevention device is controlled by the processor 305, while in other embodiments the tamper prevention device is controlled by the operations center.

In preferred embodiments, at least one output device 340 is a Radio-Frequency Identification (RFID) device. The RFID device can broadcast information about the device it is attached to. For example, the RFID device may broadcast manufacturer information, location information, last service date, device information (e.g. make, model, and/or year), current status (e.g. a valve can broadcast if it is open or closed), etc. In preferred embodiments the RFID device is updateable by the processor 305 or by the operations center. The RFID device can be either an active (e.g. battery powered) or passive (e.g. require an external source to provoke signal transmission) device.

EXAMPLES

A system of the invention is monitoring a water distribution infrastructure. The system is used to automatically control the water pressure within the system. Such a system includes a number of water meters disbursed throughout the infrastructure relaying real time use information to a control center. Upon a determination by the operations center that there is low usage of the system (e.g. at night) based on information received by a predetermined number of the water meters, the operations center causes pumps supplying pressure within the system to reduce or cease pumping. Thereby cutting down on the electricity used by the pumps while maintaining enough pressure throughout the infrastructure to satisfy any water needs. The determination to reduce or cease pumping can be also based on information received from pressure sensors disbursed throughout the infrastructure. For example, if the pressure within the infrastructure exceeds a threshold value, the operations center causes the pumps to reduce or cease pumping.

In another example, the system is used to assist in maintaining the infrastructure. Water pipes and valves are often buried underground making it difficult to locate, assess the status of the devices, and repair them if necessary. Using an example of the above described system, each device is equipped with a monitoring the device. The monitoring device, for example, may monitor for corrosion using a corrosion monitor, geographical location using a GPS receiver, and leaks using a leak detector. Upon detection of corrosion and/or a leak, the monitoring device sends a message to the operations center where the information is analyzed. The operations center is able to make a determination if the corrosion and/or leak is severe enough to warrant fixing, if the corrosion and/or leak should be watched to determine if it worsens, or if the corrosion and/or leak can be ignored. The operations center will also alert a person of the situation for further assessment.

If it is determined that the corrosion and/or leak should be fixed, the operations center disseminates information to a repair crew and redirects water flow away from the device. Such information can include location of the device, based on data received the GPS receiver, problem associated with the device, device information (e.g. make, model, and/or year), etc. The monitoring device can also be equipped with a RFID transmitter, which transmits at least, some of the above information. The repair crew receives the information on a smart phone, a portable computer, or other device capable of receiving such information. Upon completion of the repair, the operations center updates the system to indicate a new last repaired date for the device.

In another Example, the system is monitored by several entities within a municipality at the same time. For example, a fire department, a gas utility, a water utility, an electric utility, and traffic control center all monitor the system concurrently. Upon detection of smoke by a monitoring device, the control center alerts each entity of a potential fire. The location of the potential fire is determined by cross-referencing the ID number of the monitoring device with a lookup table or based on information received from a GPS receiver. The fire department uses the location information to send out emergency response personnel to the vicinity of the potential fire. The gas utility uses the location information to divert or shut off gas flow to the vicinity of the potential fire. The water utility uses the location information to divert water to or increase water pressure in the vicinity of the potential fire as well as determines if any fire hydrants in the vicinity of the potential fire are potentially damaged (e.g. are tilted at an unusual angle, are receiving no or little water pressure, or have been tampered with) based on information received from monitoring devices attached to the fire hydrants. The location of the fire hydrants is determined by cross-referencing the ID number of the monitoring device with a lookup table or based on information received from a GPS receiver. The water utility automatically alerts the fire department as to which fire hydrants to use. The water utility also disables any tamper prevention devices associated with the fire hydrants. The electric utility receives a signal that additional pressure may be needed within the water system and provides an increased electrical load to the water pumps. Additionally, the traffic control center adjusts traffic lights en route from the fire station to the vicinity of the potential fire to assist the fire trucks in arriving quickly and safely.

In another example, the system is used to monitor contamination of the fluid flowing through the system. The system includes pressure sensors, leak detectors and contamination detectors. Leaks within the system can cause a pressure drop throughout the system which can lead to contaminants being drawn into the system. For example, if a pipe is under water and the pressure inside the pipe drops below the pressure outside the pipe, the exterior water will flow into the pipe. Therefore, the system has several monitoring devices to check for such potential or actual contamination. The pressure sensors will indicate if the pressure within the system drops below a threshold level at which contaminants can be drawn into the system. The leak detectors will indicate that there is a leak through which contaminants can enter the system. While the contamination detectors will indicate if there is contamination within the system, indicating a possible breach of the infrastructure of the system.

Other embodiments and uses of the invention will be apparent to those skilled in the art from consideration of the specification and practice of the invention disclosed herein. All references cited herein, including ail publications, U.S. and foreign patents and patent applications, are specifically and entirely incorporated by reference. It is intended that the specification and examples be considered exemplary only with the true scope and spirit of the invention indicated by the following claims, furthermore, the term "comprising of" includes the terms "consisting of" and "consisting essentially of" All examples illustrate embodiments of the invention, but should not be viewed as limiting the scope of the invention.

The invention claimed is:

1. A method of disseminating information, the method comprising:
    detecting, by a first monitoring device, a first condition of a first aspect of an infrastructure and transmitting a data signal to an operations center, the data signal including data relating to the first condition and a first time stamp;
    detecting, by a second monitoring device, the first condition of the first aspect and a second condition of a second aspect of the infrastructure, and transmitting a data signal to the operations center, the data signal including data relating to the second condition and data relating to the first condition, and the data signal comprising a second time stamp;
    determining, by the operations center, whether the data included in the data signal received from either of the monitoring devices indicates a problem of contamination within the infrastructure;
    subsequent to an indication of the problem of contamination, determining, by the operations center, an amount of the contamination, an approximate location of the contamination, a direction of contamination movement, and a speed of the contamination movement, wherein the direction and the speed of the contamination movement are based on the first time stamp from the first monitoring device and the second time stamp from the second monitoring device;
    determining, by the operations center, whether the data included within the data signal received from either of the monitoring devices indicates a problem of corrosion within the infrastructure; and
    subsequent to an indication of the problem of corrosion, determining by the operations center an amount of corrosion determined to be the problem within the infrastructure and a level of severity of the corrosion;
    wherein the first aspect and the second aspect define different aspects of the infrastructure.

2. The method of claim 1, wherein each monitoring device comprises:
    at least one sensor sensing at least one of the first and second conditions within the infrastructure,
    a data storage device storing data sensed by the at least one sensor,
    a first communications device adapted to transmit and receive data, and
    a first processor communicatively coupled to the at least one sensor, the data storage device, and the first communications device.

3. The method of claim 1, wherein the second monitoring device monitors the first condition.

4. The method of claim 3, further comprising determining, by the operations center, whether a change in data between data as detected by the first monitoring device relating to the first condition from data as detected by the second monitoring device relating to the first condition indicates a second problem within the infrastructure.

5. A method of disseminating information, comprising:
    detecting, by a first monitoring device, a condition of an aspect of an infrastructure;
        transmitting, by the first monitoring device, a data signal including data relating to the condition and a first time stamp;
    detecting, by a second monitoring device, the condition of the aspect of the infrastructure;
    transmitting, by the second monitoring device, a data signal including data relating to the condition and a second time stamp;
    determining whether the data from the first monitoring device differs from the data from the second monitoring device;
    determining whether a difference in data indicates a problem of contamination within the infrastructure;
    subsequent to an indication of the problem of contamination, determining an amount of the contamination, an approximate location of the contamination, a direction of contamination movement, and a speed of the contamination movement, wherein the direction and the speed of the contamination movement are based on the first time stamp from the first monitoring device and the second time stamp from the second monitoring device;
    determining whether a difference in data indicates a problem of corrosion within the infrastructure; and
    subsequent to an indication of the problem of corrosion, determining whether the data relating to the condition as detected by the first monitoring device and the second monitoring device indicates an amount of corrosion determined to be the problem within the infrastructure, and a level of severity of the corrosion.

6. The method of claim 5, wherein the determination of a level of severity of the corrosion is performed by an operations center.

7. The method of claim 6, further comprising determining whether the corrosion is severe enough to warrant fixing based on the level of the severity of the corrosion.

* * * * *